United States Patent [19]

Detty et al.

[11] 4,450,217

[45] May 22, 1984

[54] CHALCOGENOPENTALENE COMPOUNDS IN ELECTROPHOTOGRAPHY

[75] Inventors: Michael R. Detty; Jerome H. Perlstein, both of Rochester, N.Y.

[73] Assignee: Eastman Kodak Company, Rochester, N.Y.

[21] Appl. No.: 475,675

[22] Filed: Mar. 15, 1983

[51] Int. Cl.³ .................. G03G 5/09; G03G 5/14; G03G 5/06

[52] U.S. Cl. .................. 430/58; 430/75; 430/77; 430/78; 430/83; 430/900; 260/239 R; 548/125; 548/126; 549/33; 549/36; 549/448; 549/455; 549/472; 549/479; 549/480; 549/504; 549/505

[58] Field of Search .................. 430/58, 75, 77, 78, 430/83, 900

[56] References Cited

U.S. PATENT DOCUMENTS

| | | | |
|---|---|---|---|
| 3,765,882 | 10/1973 | Virkhaus | 430/75 |
| 3,971,742 | 7/1976 | Gunther | 430/75 X |
| 4,106,934 | 8/1978 | Turnblom | 430/75 X |
| 4,329,284 | 5/1982 | Detty et al. | 430/900 X |
| 4,365,017 | 12/1982 | Detty et al. | 430/83 |

OTHER PUBLICATIONS

Journal of Chemical Society Chemical Communications, 594, (1971), Beer et al.
Journal of Chemical Society (Org.) 3187, (1976), Reed.
Journal of Chemical Society Perkin I, 2097, (1975), Reed et al.

*Primary Examiner*—Roland E. Martin, Jr.
*Attorney, Agent, or Firm*—John R. Everett

[57] ABSTRACT

Novel chalcogenopentalene compounds having a tellurium atom in the 6a position, and methods of making chalcogenopentalenes having a tellurium or a selenium atom in the 6a position are disclosed. The chalcogenopentalene compounds are useful as sensitizers in electrophotographic compositions and elements containing an electron donor and as charge emitters in multilayer photoconductive elements.

8 Claims, No Drawings

CHALCOGENOPENTALENE COMPOUNDS IN ELECTROPHOTOGRAPHY

FIELD OF THE INVENTION

This invention relates to chalcogenopentalene compounds, methods for making such compounds and electrophotographic compositions and elements comprising sensitizing amounts of such compounds.

BACKGROUND OF THE INVENTION

In photographic compositions, such as electrophotographic compositions, sensitizing compounds are often used to improve the sensitivity of the compositions. A wide variety of such compositions are in use. There exists a continuing effort to improve the performance of currently used compositions.

SUMMARY OF THE INVENTION

The present invention provides a class of chalcogenopentalene ring compounds having a selenium or tellurium atom in the 6a position which class is useful in increasing the sensitivity and quantum efficiency of electrophotographic compositions in which one component is an electron donor. This class of compounds is also useful as intermediates in forming other chalcogenopentalenes which are sensitizers for such electrophotographic compositions. All of the telluropentalenes are believed to be novel compounds.

In a preferred embodiment the chalcogenopentalene compounds of the invention have the structure

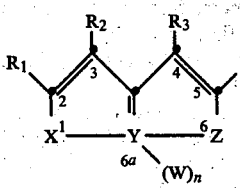

wherein
n represents 0 or 2;
X and Z each independently represents O, NR or S;
Y represents Se or Te;
W represents halogen;
R represents hydrogen, alkyl or aryl;
$R_1$, $R_2$, $R_3$ and $R_4$ each independently represents hydrogen, alkyl, aryl, substituted vinyl ($R_5CH=CH-$) or halogen; and
$R_5$ represents alkyl, aryl or a hetero group such as furfuryl, thiofuryl, pyridyl, selenofuryl, tellurofuryl; provided that when Y is Se, $R_1$, $R_2$, $R_3$ and $R_4$ are other than halogens and n is 0.

"Alkyl" refers to a branched- or straight-chained hydrocarbon having up to about 20 carbon atoms, such as methyl, butyl, dodecyl, nonyl, isobutyl, etc.; "aryl" includes phenyl, naphthyl and anthryl. Aryl and alkyl may both be substituted by other alkyl groups and substituents such as nitro, cyano, carboxy, methoxy, amino, dialkylamino, halogen and alkoxy groups.

DETAILS OF PREFERRED EMBODIMENTS OF INVENTION

The chalcogenopentalene compounds of the invention are made by a novel four step process involving condensation, conversion to a chalogenopentalene with a thio group in the 6 position, halogenation and reduction. In fact, each step of the process is considered to be independently novel and unobvious. Each step of the process also produces chalcogenopentalenes which are useful.

In the first step of the process a 3-alkyl-5-aryl-1,2-oxachalcogenol-1-ium halide is condensed with a carboxylic acid chloride, a thioacid chloride or an imidoyl chloride to form a chalcogenopentalene having an oxygen group in the 6 position and selenium or tellurium in the 6a position.

In step 2, the condensation product of step 1 is, if desired, converted to a chalcogenopentalene with a thio group in the 6 position. Step 2 is necessary since the condensation reaction of step 1 will only result in chalcogenopentalenes with —O— in the 6 position. In step 3, when the condensation product of step 1 is a telluropentalene, the condensation product may be halogenated to form novel dihalotelluropentalenes with halogen substituents in the 3 and/or 4 positions. In an alternative step 3, the product of step 2 may be similarly halogenated. In step 4 the halogenated telluro group in the product of step 3 is reduced with a compound such as hydrazine or $H_2PO_3$ to form novel 1,2-dioxa-6a-telluropentalenes. Selenapentalenes having halo substituents will not be formed in step 3.

The above method is further illustrated by the following reaction sequence for telluropentalenes:

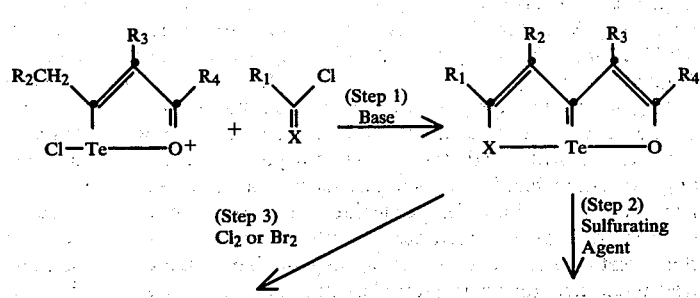

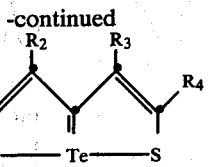
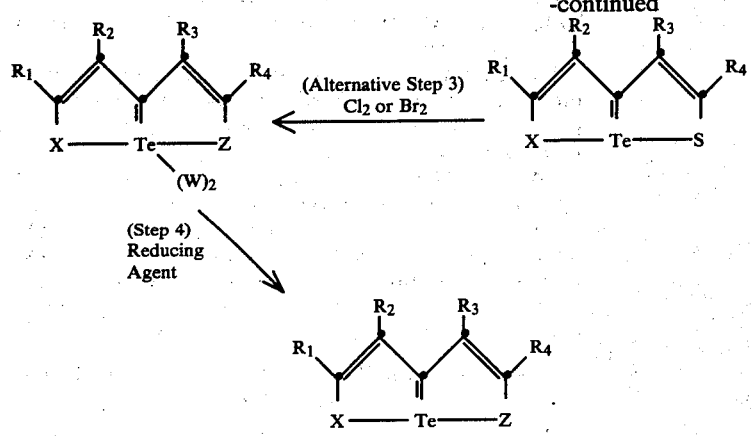

The 3-alkyl-5-aryl-1,2-oxachalcogenol-1-ium halide starting materials used in step 1 of the process are prepared by the procedure of U.S. Pat. No. 4,329,284. That procedure involves treating a 3-alkylchalcogenolacryloyl halide with a Friedel-Crafts catalyst and then isolating the resulting 3-alkyl-5-aryl-1,2-oxochalcogenol-1-ium halide. The disclosure of U.S. Pat. No. 4,329,284 is expressly incorporated herein by reference.

The carboxylic acid chloride, thioacid chloride, and imidoyl chloride starting materials are well known. Such starting materials are described in text books such as March, "Advanced Organic Chemistry:Reactions, Mechanisms and Structure" McGraw-Hill, New York, 1968 page 346. The carboxylic acid chloride and organic thioacid chloride starting materials may be obtained from the corresponding acids with standard techniques such as treating the acids with oxallyl chloride or thionyl chloride. Methods of making these materials are disclosed in standard text books such as March, "Advanced Organic Chemistry:Reactions, Mechanisms and Structure" McGraw-Hill, New York, 1968 page 346.

Examples of useful acid chloride, thioacid chlorides and imidoyl chloride materials include benzoyl chloride, acetyl chloride, anisoyl chloride, cinnamoyl chloride, p-fluorobenzoyl chloride, p-nitrobenzoyl chloride, proionyl chloride, p-cyanobenzoyl chloride, N-methylphenylimidoyl chloride, thiobenzoyl chloride, 3-(2-thienyl)acryoyl chloride, 3-(2-furanyl)acryloyl chloride, p-nitrocinnamoyl chloride.

Useful 3-alkyl-5-aryl-1,2-oxachalcogenol-1-ium halides include 3-methyl-5-phenyl-1,2-oxatellurol-1-ium chloride, 3-ethyl-5-phenyl-1,2-oxatellurol-1-ium chloride, 3-methyl-5-(p-methoxyphenyl)-1,2-oxatellurol-1-ium chloride, 3-methyl-5-(p-fluorophenyl)-1,2-oxatellurol-1-ium chloride, and 3-methyl-5-(p-N-N-dimethylaminophenyl)-1,2-oxatellurol-1-ium chloride.

Condensation reactions useful in step 1 are well known. General descriptions of such condensation techniques are described in March, "Advanced Organic Chemistry:Reactions, Mechanisms and Structure", McGraw-Hill, New York, 1968 and Detty in *Journal of Organic Chemistry*, Vol. 44, 1979, page 2073.

In general, such condensation reactions involve combining the carboxylic acid chloride, thioacid chloride or imidoyl chloride and the 3-alkyl-5-aryl-1,2-oxachalcogenol-1-ium halide in a solvent such as acetonitrile, propionitrile, or methylene chloride as a slurry or mixing the two starting materials together as a melt and then treating them with an strong organic base such as triethylamine, diisopropylethylamine, or tripropylamine. Treatment usually involves heating the mixture in the presence of the triethylamine for a period of time from about 1 minute to about 10 hours.

As stated herein before, the condensation reaction results in chalcogenopentalenes in which an —O— is in the 6th position in the ring. When a chalcogenopentalene with —S— in position 6 is desired, it is necessary to exchange —O— with —S—. This is accomplished by, in step 2, treating the condensation product of step 1 with phosphorous pentasulfide or with phosphorous pentasulfideanisole complex in toluene for 1 to 100 hours. Methods for exchanging —S— for —O— are described by Pedersen, Sheiby, Nilsson and Lawesson in *Bull. Soc. Chem. Belg.*, Vol. 79, 1978, page 223 and by Sheibye, Kristensen and Lawesson, *Tetrahedron*, Vol. 35, 1979, page 1139.

The chalcogenopentalenes resulting from condensation step 1 can be converted to 3- and/or 4-halo derivatives by the halogenation procedure of Reig in *J.C.S. Chem. Comm.*, 1972, page 1283 for thia and selenapentalenes. Halogenation (step 3) of the condensation product of step 1 or step 2 for tellurapentalenes is carried out conveniently by dissolving the starting materials in a solvent such as methylene chloride, chloroform, ether or carbon tetrachloride. The solution is cooled to a temperature of about −78° to 0° C. The selected halogen is added directly to the solution resulting in a reaction between the halogen and the starting material. The reaction is allowed to proceed from about 1 minute to 2 hours.

The reduction (step 4) of the halogenated product of step 3 of the method is generally carried out by dissolving the halogenated product in a solvent such as methylene chloride, chloroform, ether, or carbon tetrachloride. Reduction is then achieved by adding an aqueous solution of a reducing agent such as hydrazine or $H_3PO_3$ to the solution of the halogenated product.

The products of each step of the process are isolated from the reaction mixture and purified using any chemical separation method or technique for isolating and purification of chemical compounds. Such methods and techniques include drowning the crude reaction mixture with cold water, removing the product by extraction with a water-immiscible solvent such as a halogenated solvent, drying, precipitation by concentration and recrystallization from an organic solvent such as methanol when the products are solids, or separating chromatographically when the products are liquids.

The above described methods for the preparation of the chalcogenopentalene compounds of the invention are illustrated in the following examples.

EXAMPLE 1

2,5-diphenyl-1,6-dioxa-6a-telluropentalene

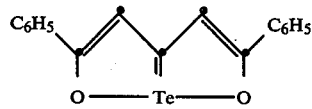

Compound 1, Table I, infra

Benzoyl chloride (0.43 g, 3.0 mmol) and 3-methyl-5-phenyl-1,2-oxatellurolium chloride (0.50 g, 1.6 mmol) were slurried in 10 ml of acetonitrile. Triethylamine (0.51 g, 5.0 mmol) in 5 ml of acetonitrile was added and the resulting mixture was warmed 10 minutes on a steam bath. The reaction mixture was concentrated and the residue was purified by chromatography on silica gel, eluting with methylene chloride. The yellow, crystalline material was recrystallized from methanol to give 0.23 g of compound 1 as yellow needles having a mp 169.5°–170.5° C.

EXAMPLE 2

2-(p-methoxyphenyl)-5-(p-nitrophenyl)-1,6-dioxa-6a-telluropentalene

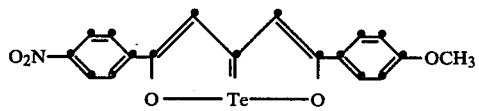

Compound 6, Table I p-Nitrobenzoyl chloride (0.96 g, 5.2 mmol) and 3-methyl-5-(p-methoxyphenyl)-1,2-oxatellurol-1-ium chloride (0.64 g, 2.0 mmol) were added to 2.0 g (20 mmol) of triethylamine. The resulting mixture was heated until a solution was obtained. Acetonitrile (5 ml) was added precipitating the product. Recrystallization from methanol gave 0.34 g of titled compound having a mp 353°–255° C.

EXAMPLE 3

2-(p-methoxyphenyl)-5-(p-nitrophenyl)-1,6-dioxa-6a-selenapentalene

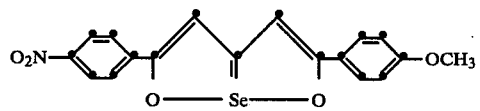

Compound 13, Table I p-Nitrobenzoyl chloride (1.50 g, 8.1 mmol) and 3-methyl-5-(p-methoxyphenyl)1,2-oxaselenol-1-ium chloride (0.81 g, 3.0 mmol) were heated until a homogeneous melt was formed. Triethylamine (4 ml) was added and the resulting mixture was heated 1 minute at 100° C. The reaction mixture was diluted with methylene chloride (100 ml). The organic phase was washed with 5 percent HCl (twice with 50 ml), was dried over magnesium sulfate, and was concentrated. The residue was recrystallized from acetonitrile to give 0.36 g of 13 as a yellow solid having a mp 244°–247° C.

EXAMPLE 4

2,5-diphenyl-1-oxa-6-thiatelluropentalene (Compound 16, Table I)

Compound 1, Table 1 (0.38 g, 1.0 mmol) was heated in 10 ml of toluene with 0.5 g of the $P_2S_5$-anisole complex

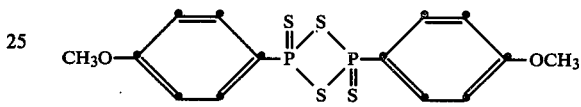

at reflux for 48 hours. The reaction mixture was cooled to room temperature and filtered through a column of 20 g of silica gel and eluted with methylene chloride. The product was recrystallized from 10 ml of acetonitrile to give 0.30 g of crystalline material having a melting point of 168°–170° C.

EXAMPLE 5

N-methyl-2,5-diphenyl-1-aza-6-oxatelluropentalene (Compound 22, Table I)

N-methyl phenylimidoyl chloride (0.46 g, 3.0 mmol) and 3-methyl-5-phenyl-1,2-oxatellurolium chloride (0.50 g, 1.6 mmol) were slurried in 10 ml of acetonitrile. Triethylamine (0.51 g, 5.0 mmol) in 5 ml of acetonitrile was added and the resulting mixture was warmed 10 minutes on a steam bath. The reaction mixture was concentrated and the residue was purified by chromatography on silica gel, eluting with methylene chloride. The yellow, crystalline material was recrystallized from acetonitrile to give 0.25 g of Compound 22, Table 1 as a yellow solid, mp 98°–100° C.

Table I presents chalcogenopentalene compounds 1–16 and 19–22 made according to the described step 1 condensation method. The structure of each compound of the table was confirmed by NMR analysis, infrared spectral analysis, mass spectral analysis and elemental analysis. In the table, Ph represents phenyl and Me represents methyl.

TABLE I

| Compound No. | Compound | mp, °C. |
|---|---|---|
| 1. | Ph—[structure]—Ph, O—Te—O | 169.5–170.5 |

TABLE I-continued

| Compound No. | Compound | mp, °C. |
|---|---|---|
| 2. | 4-O₂N-C₆H₄-CH=C(-O-Te-O-)CH=CH-Ph (cyclic tellurium diketonate) | 202–206 |
| 3. | 4-CH₃O-C₆H₄-CH=C(-O-Te-O-)CH=CH-Ph | 183–185 |
| 4. | CH₃-C(-O-Te-O-)=CH-CH=C-Ph | 142–144 |
| 5. | 4-O₂N-C₆H₄-CH=C(-O-Te-O-)CH=CH-C₆H₄-4-NMe₂ | 184–186 |
| 6. | 4-O₂N-C₆H₄-CH=C(-O-Te-O-)CH=CH-C₆H₄-4-OCH₃ | 253–255 |
| 7. | 4-CH₃O-C₆H₄-CH=C(-O-Te-O-)CH=CH-C₆H₄-4-OCH₃ | 250–251 |
| 8. | CH₃-C(-O-Te-O-)=CH-CH=C-C₆H₄-4-OCH₃ | 163–165 |
| 9. | Ph-C(-O-Te-O-)=CH-CH=C-C₆H₄-4-F | 207–209 |
| 10. | 4-O₂N-C₆H₄-CH=C(-O-Te-O-)CH=CH-C₆H₄-4-F | 227–228 |

TABLE I-continued

| Compound No. | Compound | mp, °C. |
|---|---|---|
| 11. | 4-CH₃O-C₆H₄-CH=CH-C(=O)-CH=CH-C₆H₄-4-F (Te chelate, O—Te—O) | 208.5–210.5 |
| 12. | CH₃-C(=O)-CH=CH-C(=O)-CH=CH-C₆H₄-4-F (Te chelate, O—Te—O) | 112–114 |
| 13. | 4-O₂N-C₆H₄-CH=CH-C(=O)-CH=CH-C₆H₄-4-OCH₃ (Se chelate, O—Se—O) | 244–247 |
| 14. | 4-CH₃O-C₆H₄-CH=CH-C(=O)-CH=CH-C₆H₄-4-OCH₃ (Se chelate, O—Se—O) | 251–253 |
| 15. | 4-O₂N-C₆H₄-CH=CH-C(=O)-CH=CH-C₆H₄-4-F (Se chelate, O—Se—O) | 250–251 |
| 16. | Ph-C(=O)-CH=CH-C(=S)-Ph (Te chelate, O—Te—S) | 168–170 |
| 17. | Ph-C(=O)-C(Cl)=CH-C(=O)-Ph (Te chelate, O—Te—O) | 150.5–152.5 |
| 18. | Ph-C(=O)-C(Br)=CH-C(=O)-Ph (Te chelate, O—Te—O) | 166–167.5 |
| 19. | 2-furyl-C(=O)-CH=CH-C(=O)-CH=CH-C₆H₄-4-F (Te chelate, O—Te—O) | 166–167.5 |
| 20. | 2-thienyl-C(=O)-CH=CH-C(=O)-CH=CH-C₆H₄-4-F (Te chelate, O—Te—O) | 166–167.5 |

TABLE I-continued

| Compound No. | Compound | mp, °C. |
|---|---|---|
| 21. | (structure with CH2CH2CH2CH3 chain attached to phenyl, with O—Te—O bridge and Ph group) | 107–110 |
| 22. | (structure with two Ph groups, N(CH3)—Te—O bridge) | 98–100 |

Other representative compounds which can be made according to the method of the invention include:

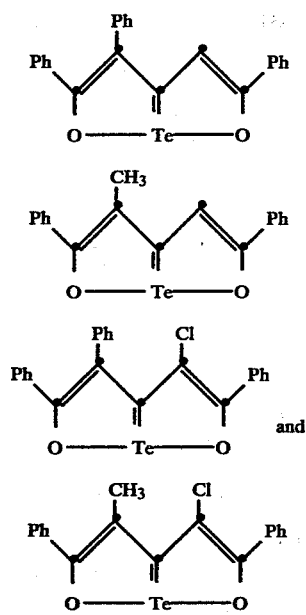

Examples 6 and 8 illustrate the halogenation steps for making dihaloteIluropentalenes. Examples 7 and 9 illustrate the reduction step for making 2, and/or 5-substituted telluropentalenes.

EXAMPLE 6

2,5-diphenyl-4-bromo-1,6-dioxa-6a-dibromotelluropentalenes (Compound 24, Table II)

Compound I, Table I (0.19 g, 0.50 mmol) was dissolved in 50 ml of methylene chloride. The resulting solution was cooled to −40° C. and bromine (0.20 g, 1.2 mmol) was added giving a magenta solution. The reaction mixture was stirred 1 minute at −40° C. and was then concentrated. The residue was recrystallized from 50 ml of boiling chloroform to give 0.20 g (70%) of small, green needles, mp 198°–198.5° C. identified as the titled compound.

EXAMPLE 7

Preparation of 3-bromo-2,5-diphenyl-1,6-dioxa-6a-tellurapentalene (Compound 18, Table I)

Compound 24, Table II prepared in Example 4 was dissolved in 20 ml of methylene chloride. Aqueous hydrazine (64°/solution 0.5 ml) was added with stirring. The reaction mixture was diluted with 20 ml of water. The organic phase was separated, dried over sodium sulfate and concentrated to give a red-brown solid. Recrystallization from acetonitrile gave 0.10 g (71%) of compound 18 of Table I, mp 166°–167.5° C.

EXAMPLE 8

2,5-diphenyl-3-chloro-1,6-dioxa-dichlorotelluropentalene (Compound 27, Table II)

Compound 1, Table 1 (0.12 g, 0.33 mmol) was dissolved in 50 ml of methylene chloride. The resulting solution was cooled to −70° and 0.035 g (0.50 mmol) of chlorine was added. The resulting solution was concentrated. The residue was recrystallized from acetonitrile to give 0.090 g (57%) of the titled compound as a green crystalline solid, mp 186°–192° C.

EXAMPLE 9

Preparation of 3-chloro-2,5-diphenyl-1,6-dioxa-6a-telluropentalene (Compound 17, Table I)

Compound 27 prepared in Example 6 (0.048 g, 0.10 mmol) was dissolved in 10 ml of methylene chloride and 0.5 ml of 64% aqueous hydrazine was added. The reaction mixture was washed with water (10 ml), dried over sodium sulfate and concentrated. The residue was recrystallized from acetonitrile to give 0.036 g (89%) of compound 17 of Table 1, mp 150.5°–152.5° C.

Other dihalotelluropentalenes having a dihalotellurium group in position 6a are presented in Table II.

TABLE II

1,6-Dioxa-6a-dihalotelluropentalene

| Compound No. | Compound | CH$_2$Cl$_2$ λ max, nm | mp, °C. |
|---|---|---|---|
| 27. | Ph–C(O–Te(Br)(Br)–O)=CH–...–CH=C–Ph | 547 | 229–230 |
| 28. | Ph–C(O–Te(Br)(Br)–O)=C(Br)–...–CH=C–Ph | 555 | 198–198.5 |
| 29. | (4-F-C$_6$H$_4$)–C(O–Te(Br)(Br)–O)=CH–...–CH=C–(4-F-C$_6$H$_4$) | 585 | 202–205 |
| 30. | (4-F-C$_6$H$_4$)–C(O–Te(Cl)(Cl)–O)=C(Cl)–...–C(Cl)=C–(4-F-C$_6$H$_4$) | 587 | 212–215 |
| 31. | Ph–C(O–Te(Cl)(Cl)–O)=C(Cl)–...–CH=C–Ph | 548 | 186–192 |
| 32. | Ph–C(O–Te(Cl)(Cl)–O)=C(Cl)–...–C(Cl)=C–Ph | 544 | 178–180.5 |
| 33. | (4-Me-C$_6$H$_4$)–C(O–Te(Br)(Br)–O)=CH–...–C(Br)=C–(4-NMe$_2$-C$_6$H$_4$) | 593 | >330 |
| 34. | (4-O$_2$N-C$_6$H$_4$)–C(O–Te(Br)(Br)–O)=CH–...–C(Br)=C–(4-NMe$_2$-C$_6$H$_4$) | 590 | >330 |

TABLE II-continued
1,6-Dioxa-6a-dihalotelluropentalene

| Compound No. | Compound | CH$_2$Cl$_2$ λ max, nm | mp, °C |
|---|---|---|---|
| 35. | 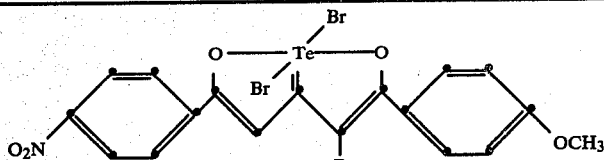 | 555 | 212–215 |
| 36. | 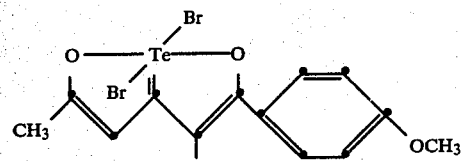 | 538 | 192–193 |
| 37. | 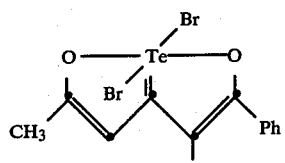 | 528 | 174–177 |
| 38. | 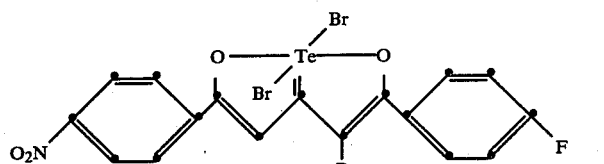 | 555 | 195–196 |

The present invention provides photoconductive elements in which electron donating compounds (p-type photoconductors) are combined with sensitizing amounts of the chalcogenopentalenes. These compositions and elements are useful in electrophotographic processes. Such processes employ a photoconductive element comprising a support material having thereon a coating containing a photoconductive composition. The element is first given a uniform surface charge after a suitable period of dark adaptation. The element is then exposed to a pattern of actinic radiation which has the effect of differentially reducing the potential of the surface charge in accordance with the relative energy contained in various parts of the radiation pattern. The differential surface charge or electrostatic latent image remaining on the element is then made visible by contacting the surface with a suitable electroscopic marking material (toner). Such marking material, whether contained in an insulating liquid or on a dry carrier, is deposited on the exposed surface in accordance with either the charge pattern or the absence of charge pattern as desired. The deposited marking material is then either permanently fixed to the surface of the sensitive element by known means such as heat, pressure and solvent vapor, or transferred to a second element to which it is similarly fixed. Similarly, the electrostatic latent image can be transferred to a second element and developed there.

The photoconductive elements are generally prepared by blending a dispersion or solution of the electron-donor together with an electrically insulating, film-forming resin binder, when necessary or desirable, and coating the composition on a support or forming a self-support layer of the photoconductive composition. A sensitizing amount of the chalcogenopentalene compound is mixed with the donor composition so that, after thorough mixing and drying, the chalcogenopentalene compound is uniformly distributed throughout a layer formed from the composition. The amount of sensitizer which can be added to a photoconductive composition layer to give effective increases in sensitivity can vary widely. The optimum concentration in any given case will vary with the specific donor and specific compound of the invention. Preferred compositions comprise from 0.1 to 10 weight percent of the chalcogenopentalene and 10 to 40 weight percent of the electron donor.

The chalcogenopentalenes of the invention are also useful in so-called multi-active photoconductive elements. Such elements have at least two layers comprising an organic electron donating, charge-transport layer in electrical contact with a charge-generation layer comprising the chalcogenopentalene. Both the charge-generation layer and the charge-transport layer may include a binder. The layers may also be vacuum deposited without a binder. The charge-transport layer contains, as the active charge-transport material, one or more organic electron donors capable of accepting and transporting charge carriers generated by the charge-generation layer.

Such multi-active elements are well known in the electrophotographic art and thus need not be discussed in detail here. Berwick et al's U.S. Pat. No. 4,175,960 issued Nov. 27, 1979 described in detail an especially useful arrangement for multi-active elements. The disclosure of Berwick et al is expressly incorporated herein by reference.

The chalcogenopentalene compounds are effective for enhancing the photosensitivity of a wide variety of electron-donating photoconductors. Useful electron donors include:

1. arylamine photoconductors including substituted and unsubstituted arylamines, diarylamines, nonpolymeric triarylamines and polymeric triarylamines such as those described in U.S. Pat. Nos. 3,240,597 by Fox, issued Mar. 15, 1966 and 3,180,730 by Klupfel et al, issued Apr. 27, 1965;
2. polyarylalkane photoconductors of the types described in U.S. Pat. Nos. 3,274,000 by Noe et al, issued Sept. 20, 1966; 3,542,547 by Wilson, issued Nov. 24, 1970 and 3,542,544 by Seus et al, issued Nov. 24, 1970;
3. 3-diarylamino-substituted chalcones of the types described by Fox, U.S. Pat. No. 3,526,501 issued Sept. 1, 1970;
4. nonionic cycloheptenyl compounds of the types described by Looker, U.S. Pat. No. 3,533,786 issued Oct. 13, 1970;
5. compounds containing an: $>N-N<$ nucleus, as described by Fox, U.S. Pat. No. 3,542,546 issued Nov. 24, 1970;
6. organic compounds having a 3,3'-bisaryl-2-pyrazoline nucleus, as described by Fox et al, U.S. Pat. No. 3,527,602 issued Sept. 8, 1970;
7. triarylamines in which at least one of the aryl radicals is substituted by either a vinyl radical or a vinylene radical having at least one active hydrogen-containing group, as described by Brantly et al, U.S. Pat. No. 3,567,450 issued Mar. 2, 1971;
8. triarylamines in which at least one of the aryl radicals is substituted by an active hydrogen-containing group, as described by Brantly et al, Belgian Pat. No. 728,563 dated Apr. 30, 1971;
9. any other organic electron donor compound which exhibits photoconductive properties such as those set forth in Australian Pat. No. 248,402 and the various polymeric photoconductors such as the photoconductive carbazol polymers described in U.S. Pat. No. 3,421,891, issued Jan. 14, 1969.

The following examples illustrate the use of chalcogenopentalenes as sensitizers in electrophotographic compositions and elements containing electron donating photoconductors. Each element was formulated and coated as follows.

EXAMPLES 10-14

An electrophotographic element was prepared by first dissolving sufficient quantities of the chalcogenopentalene and tri-p-tolylamine in dichloromethane (DCM) to provide a dried layer containing 2.0% by weight of the selected chalocogenopentalene and 30% by weight of the tri-p-tolylamine. A sufficient amount of a stock solution containing Lexan 145 TM polycarbonate (General Electric) in DCM was added to the solution to obtain a dried layer comprising about 68% by weight of Lexan 145 TM. The solution was stirred for several minutes and then coated at 0.006 mil (0.015 mm) wet thickness on a poly(ethylene terephthalate) support containing 0.4 OD evaporated nickel. After initial evaporation of the solvent, the elements were dried 24 hours in air at 60° C. Dry thickness was about 7 μm.

The quantum efficiency of each element was measured as follows. Samples were corona-charged to a surface potential equivalent to the field strengths, $E_o$, indicated in Table II. They were then exposed to monochromatic radiation at λ=350 nm with a bandwidth of 10 nm. The incident photon flux (I) at 350 nm was measured witth an Optronics Laboratories Model 730-A Radiometer. Films were allowed to discharge while exposed to the 350 nm radiation. The initial quantum efficiency $\phi_o$, (the number of electron-hole pairs produced per incident photon) at field strength $E_o$ was then determined from the relation:

$$\phi_o = (\kappa\epsilon_o/eId)\cdot(dV/dt)$$

wherein
κ is the film dielectric constant of 3,
$\epsilon_o$ is the permitivity of free space constant $8.85419 \times 10^{-12}$ coulombs $^2$/Newton Meters$^2$
e is the electronic charge constant $1.6022 \times 10^{-19}$ coulombs,
I is the incident photon flux,
d is the thickness of the film in meters, and
dV/dt is the slope of the discharge curve at $E_o$.

The photodischarge sensitivity at 350 nm, $S_{\frac{1}{2}}$, was also determined by allowing the elements to discharge from $E_o$ to $E_o/2$. The amount of radiation necessary to produce this discharge was then calculated from the time required for this half-decay and the incident photon flux.

Table III shows the quantum efficiencies ($\phi_o$) at $E_o$ and photosensitivity ($S_{\frac{1}{2}}$) for ten different electrophotographic elements. In general, the chalcogenopentalene increases the initial quantum efficiency and/or the photosensitivity of the elements compared to a control element which does not contain a chalcogenopentalene.

TABLE III

Quantum Efficiency $\phi_o$, and Photosensitivity, of Electrophotographic Elements Containing Chalcogenopentalene Compounds

| Example No. | Compound | λ, nm | $E_o$, V/cm | $\phi_o$ | $S_{\frac{1}{2}}$, ergs/cm$^2$ |
|---|---|---|---|---|---|
| control | none | 350 | $1.6 \times 10^6$ | 0.0094 | 1500 |
| 10 | 2 | 425 | $7.6 \times 10^5$ | 0.013 | 275 |
| 11 | 3 | 350 | $1.0 \times 10^6$ | 0.012 | 391 |
| 12 | 5 | 350 | $6.7 \times 10^5$ | 0.03 | 92 |
| 13 | 6 | 350 | $9.9 \times 10^5$ | 0.067 | 50 |
| 14 | 9 | 350 | $1.0 \times 10^6$ | 0.016 | 372 |
| 15 | 10 | 350 | $9.9 \times 10^5$ | 0.124 | 39 |
| 16 | 13 | 350 | $9.9 \times 10^5$ | 0.11 | 34 |
| 17 | 14 | 350 | $1.0 \times 10^6$ | 0.0084 | 538 |
| 18 | 15 | 350 | $1.0 \times 10^6$ | 0.10 | 56 |
| 19 | 17 | 300 | $1.0 \times 10^6$ | 0.025 | 367 |

EXAMPLES 20-27

These examples illustrate the utility of the chalcogenopentalenes of the invention in so called multi-active or two layer electrophotographic elements. Eight different elements were prepared as follows.

For each element a thin film of a chalcogenopentalene was vacuum deposited onto a conducting layer from a resistance heated silicon monoxide crucible using a vacuum coating system Model 3117 manufactured by Varian Associates, Inc. The resulting layers were from 100 to 1000 Å thick.

Next, the chalcogenopentalene crucible was replaced with a crucible containing 1,1-bis(4-di-p-tolylaminophenyl) cyclohexane. The conducting layer was maintained in position. After evacuation and initial crucible heating, a crystalline film of 1,1-bis(4-di-p-tolylaminophenyl) cyclohexane was vacuum deposited to a thickness of from 1 to 9μ at a deposition rate of about 200 Å/sec on the open surface of the previously deposited chalcogenopentalene layer.

The photodischarge sensitivity measured at various wavelengths was determined as in Examples 8-17. The results are presented in Table IV. In general, the photodischarge sensitivity of the two layer element is improved compared to a control which contained the vacuum deposited 1,1-bis(4-di-p-tolylaminophenyl) cyclohexane only.

TABLE IV

Photosensitivity, $S_j$, for Chalcogenopentalenes in a Multi-Active Photoconductive Element

| Example No. | Table I Compound | λ, nm | Conductive* Layer | $E_o \times 10^{-5}$ V/cm | $S_j$, ergs/cm² |
|---|---|---|---|---|---|
| 20 | 2 | 380 | A | 3.3 | 47 |
| 21 | 3 | 380 | A | 3.6 | 56 |
|  |  | 380 | B | 6.7 | 51 |
|  |  | 380 | C | 6.7 | 74 |
| 22 | 6 | 430 | A | 1.6 | 7 |
|  |  | 430 | C | 6.7 | 17 |
| 23 | 8 | 390 | A | 2.8 | 627 |
|  |  | 390 | C | 1.6 | 579 |
| 24 | 9 | 380 | A | 3.0 | 341 |
|  |  | 380 | C | 6.7 | 621 |
| 25 | 12 | 390 | A | 4.2 | 869 |
|  |  | 390 | C | 4.0 | 2463 |
| 26 | 13 | 390 | B | 8.9 | 169 |
| 27 | 14 | 430 | B | 8.9 | 110 |

*A = aluminum on Estar, B = CuI on cellulose nitrate, C = a coating of an organic dark conductor comprising tetrahydronaphthotetrathiofulvalene.TCNQ complex in a polymeric binder.

The invention has been described in detail with particular reference to preferred embodiments thereof, but it will be understood that variations and modifications can be effected within the spirit and scope of the invention.

We claim:

1. A multi-active electrophotographic element comprising a conductive support having thereon a charge generation layer containing a chalcogenopentalene having a tellurium or a selenium atom in the 6a position in electrical contact with a charge transport layer containing an electron donor.

2. An electrophotographic element comprising a conductive support and a layer of an electrophotographic composition characterized in that the composition comprises an electron donor photoconductor, and a sensitizing amount of a chalcogenopentalene having a tellurium or a selenium atom in the 6a position.

3. The element of claim 2 or 1 wherein the chalcogenopentalene has the structure

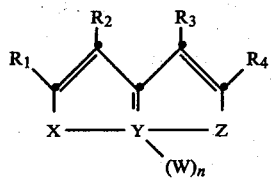

wherein
n represents 0 or 2;
X and Z each independently is O, NR or S;
Y represents Se or Te;
W represents halogen;
R is hydrogen, alkyl or aryl;
$R_1$, $R_2$, $R_3$ and $R_4$ each independently is hydrogen, alkyl, aryl, substituted vinyl having the formula $R_5CH=CH-$ or halogen; and
$R_5$ is alkyl, aryl or a hetero group.

4. The element of claim 2 or 1 wherein the chalcogenopentalene is selected from Table I.

5. The element of claim 1 wherein both the charge-generation layer and the charge-transport layer are vacuum deposited without a binder.

6. An electrophotographic composition comprising an electron donating organic photoconductor, and a sensitizing amount of a chalcogenopentalene having a tellurium or a selenium atom in the 6a position.

7. The composition of claim 6 wherein the chalcogenopentalene has the structure

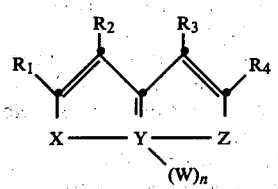

wherein
n represents 0 or 2;
X and Z each independently is O, NR or S;
Y represents Se or Te;
W represents halogen;
R is hydrogen, alkyl or aryl;
$R_1$, $R_2$, $R_3$ and $R_4$ each independently is hydrogen, alkyl, aryl, substituted vinyl($R_5CH=CH-$) or halogen; and
$R_5$ is alkyl, aryl or a hetero group; provided that when Y is Se, then $R_1$, $R_2$, $R_3$ and $R_4$ is other than halogen and n is 0.

8. The compositions of claim 6 wherein the chalcogenopentalene is selected from Table I.

* * * * *